United States Patent [19]

Smolin et al.

[11] Patent Number: 4,687,843
[45] Date of Patent: Aug. 18, 1987

[54] ESTERIFIED PROPOXYLATED GLUCOSE COMPOSITIONS

[75] Inventors: Martin Smolin, Edison; Stuart B. Polovsky, Matawan, both of N.J.

[73] Assignee: Amerchol Corporation, Edison, N.J.

[21] Appl. No.: 833,818

[22] Filed: Feb. 26, 1986

Related U.S. Application Data

[63] Continuation of Ser. No. 755,632, Jul. 16, 1985, abandoned.

[51] Int. Cl.$^4$ .................. A61K 7/42; A61K 31/78; A61K 35/12; C07H 15/00
[52] U.S. Cl. .................. 536/18.3; 536/18.2; 514/845; 514/846; 514/847; 514/873
[58] Field of Search ............ 536/41, 18.2, 18.3, 536/119; 514/25, 845, 846, 847, 873

[56] References Cited

U.S. PATENT DOCUMENTS

| | | | |
|---|---|---|---|
| 3,585,185 | 6/1971 | Levis, Jr. et al. | 536/18.2 |
| 3,655,645 | 4/1972 | Jacques | 536/18.3 |
| 4,151,304 | 4/1979 | Evans | 536/119 |
| 4,364,930 | 12/1982 | Griat et al. | 536/18.2 |

Primary Examiner—Ronald W. Griffin
Attorney, Agent, or Firm—Henry H. Gibson

[57] ABSTRACT

An esterified propoxylated methyl glucoside composition is prepared by reacting a propoxylated methyl glucoside with a fatty acid at an elevated temperature in the presence of an acid catalyst. The esterified propoxylated methyl glucoside compositions find use as skin moisturizers and emollients which are especially suitable in skin care formulations.

38 Claims, No Drawings

ESTERIFIED PROPOXYLATED GLUCOSE COMPOSITIONS

CROSS REFERENCE TO RELATED APPLICATION

This application is a continuation of application Ser. No. 755,632 filed July 16, 1985 and now abandoned.

BACKGROUND OF THE INVENTION

1. Field of the Invention

The present invention relatess to esterified propoxylated methyl glucoside compositions having utility as skin moisturizers and emollients.

2. Description of the Prior Art

The development of moisturizers to maintain the skin in a soft, supple, and elastic condition has been a major objective and the subject of substantial research and investigation in the cosmetic industry.

One of the first studies in this area was by Blank, I. H. "Factors Which Influence the Water Content of the Stratum Corneum", J. Invest. Dermatol., Vol. 18, page 433 (1952).

For many years sugar has been studied as the building block for new derivatives with useful properties in cosmetic and dermatological preparations. See Seldner, A. "Glucose Derivatives in Emollient Skin Care Formulations", Cosmetics and Toiletries, Vol. 93, No. 3, pp 73-75 (March 1978); Seldner, A., "Methyl Glucoside Ethers and Esters in Cosmetic Creams and Lotions", Cosmetics and Toiletries, Vol. 95, No. 3, pp 85-86 (March 1980); Conrad, L. I., "New Glucose Derivatives in Skin Lotions", Cosmetics and Perfumery (March 1974); Deshpande, V. M. et al, "Potential New Skin-Care Humectants: An Evaluation", Cosmetic Technology, Vol. 2, No. 9, pp 20-30 (September 1980).

The use of glucose derivatives has also found application in perfumes as disclosed by Moshel, H. et al, "Demonstrating Perfume Fixation", Perfumer & Flavorist, Vol. 7, pp 41-47 (April/May 1982) and Seldner, A., "Fragrance: Basics for the Formulating Chemist", Cosmetic Technology, pp 70-75 (June 1980). The use of glucose derivatives in soaps is disclosed by Pavlichko, J. P. et al, "Improving Emollience and Reducing Cracking in Skin Soaps", Cosmetic Technology (June 1981). The use of glucose derivatives in conditioners and fixatives is disclosed by Fleischner, A. M. et al, "Lanolin and Glucose Derivatives in Conditioners and Fixatives", Cosmetics and Toiletries, Vol. 94, No. 3, pp 69-70 (March 1979). The use of glucose derivatives in shampoos is disclosed by Fleischner, A. M. et al, "Lanolin and Glucose Derivatives in Shampoos", Cosmetics and Toiletries, Vol. 94, No. 6, pp 57-58 (1979).

An article by Otey, F. H. et al, "The Preparation and Properties of Polyoxyethylene Methyl Glucoside Fatty Esters", The Journal of the American Oil Chemists Society, Vol. 38, pp 517-520 (October 1961) discloses etherification of polyoxyethylated methyl glucoside .esters of some saturated and unsaturated fatty acids for anticipated applications in the preparation of emulsion paints.

The patent literature also discloses substantial development work in sugar chemistry for various applications. For example, U.S. Pat. No. 3,655,645 to Jacques et al, discloses the simultaneous reaction of one or more organic substances having one or more functional groups with a shiftable hydrogen, such as glucose are simultaneously reacted with one or more organic substances with acid character and/or mineral salts or anhydrides, and one or more oxyalkylation substances, with or without solvent to obtain plastifying or drying compositions.

U.S. Pat. No. 4,011,389 to Langdon, discloses a method for making glycoside polyethers by reacting glucose with an alcohol containing up to 4 carbon atoms to obtain a glycoside more lipophilic than glucose, and then reacting the glycoside with a hydrophobic oxirane-containing material for the purpose of making non-ionic surfactants.

U.S. Pat. No. 4,137,401 to Lemieux, discloses a method for synthesizing carbohydrate antigenic determinants in a form suitable for linkage to carrier molecules or solid supports. The compounds produced are glycoside-ether-esters.

U.S. Pat. No. 4,268,498 to Gedeon et al, discloses cosmetic sticks which incorporate polyoxyethylene glucose fatty acid ester. The cosmetic sticks can accommodate cosmetically acceptable ingredients such as fragrances and sunscreens.

U.S. Pat. No. 4,364,930 to Griat et al, discloses cosmetic emulsions containing carboxylates of alpha-methyl glucoside polyoxyethylenated with 10 to 30 moles of ethylene oxide. These compositions can be used for various products in the form of creams, balms, ointments and the like.

SUMMARY OF THE INVENTION

The present invention relates to esterified propoxylated methyl glucoside compositions. The esterified propoxylated methyl glucoside compositions find use as skin moisturizers and emollients which are especially suitable in skin care formulations. The esterified propoxylated methyl glucoside compositions are obtained by propoxylating methyl glucoside and then reacting the propoxylated product with a fatty acid to obtain the esterified propoxylated methyl glucoside compound.

DESCRIPTION OF THE PREFERRED EMBODIMENTS

In accordance with the present invention, the esterified propoxylated methyl glucoside is prepared by reacting a propoxylated methyl glucoside having the following structural formula:

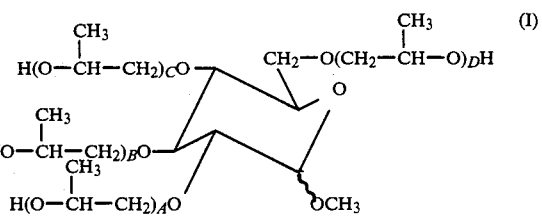

wherein $A+B+C+D$ ranges from about 5 to 50, preferably about 10 to 20, with a fatty acid at an elevated temperature in the presence of an acid catalyst to produce the esterified propoxylated methyl glucoside having the structural formula:

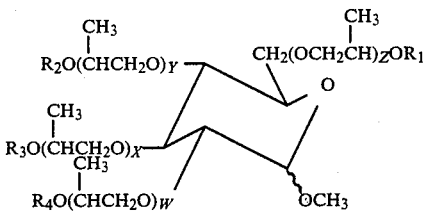

(II)

wherein the sum of W+X+Y+Z represents the average mole ratio of propylene oxide to methyl glucoside in the propoxylate, and varies from about 5 to 50, preferably about 10 to 20, and wherein any one of $R_1$, $R_2$, $R_3$ and $R_4$ can be H or

wherein M is $C_{11}$–$C_{29}$ alkyl or alkenyl, and at least one of $R_1$, $R_2$, $R_3$ and $R_4$ is

The $C_{11}$–$C_{29}$ alkyl or alkenyl groups may be derived from fatty acids.

The fatty acid can be stearic acid, linoleic acid, oleic acid, lauric acid, palmitic acid, linolenic acid, and linseed oil acid, or mixtures thereof. The fatty acid is preferably stearic acid or oleic acid, and most preferably stearic acid.

Certain specific propoxylated methyl glucosides can be obtained commercially from Amerchol Corp., Edison, N.J., under the trademark Glucam ® P-20 or Glucam ® P-10. Glucam ® P-20 has been assigned the name PPG-20 Methyl Glucose Ether by the Cosmetic, Toiletry and Fragrance Association (CTFA) and a Chemical Abstracts Service (CAS) Registry No. 61849-72-7. Glucam ® P-10 has been assigned the name PPG-10 Methyl Glucose Ether by the CTFA and the same CAS Registry No. 61849-72-7.

The acid catalyst can be toluene sulfonic acid, sulfuric acid, phosphoric acid, $SO_2$, $H_3BO_3$, a Lewis acid such as $BF_3$ or $AlCl_3$, and organic acids, such as oxalic acid. The preferred acid catalyst is toluene sulfonic acid, most preferably p-toluene sulfonic acid. The amount of acid catalyst should be sufficient to complete the esterification reaction within about 2 to 15 hours. Generally amounts of 0.5 to 2 weight % catalyst, based on the total weight of the reaction mixture is sufficient.

The esterification reaction is conducted under an inert atmosphere using such gases as nitrogen, helium and argon to blanket the reaction, with nitrogen being the preferred inert gas.

The components of the reaction mixture are contacted, by such means as stirring, at temperatures of about 50°–90° C., with about 70°–75° C. being preferred. Heating is continued until intimate admixture and homogeneity of the reaction mixture occurs.

The reaction mixture containing the propoxylated methyl glucoside, organic acid and catalyst is heated to a temperature of about 100° to 120° C., preferably under vacuum in the range of about 5 to 10 mm Hg, to distill water vapor formed during the esterification reaction.

An inert gas sparge using a gas such as nitrogen, argon or helium, and preferably nitrogen, can be maintained to facilitate the distillation and removal of water vapor. Most preferably, the distillation is conducted at a temperature of about 110° C. until the acid value of the reaction mixture is below 5 and preferably below 4, depending upon the degree of esterification. This can take from about 2 to 15 hours.

Acid value is defined as milligrams of potassium hydroxide required to neutralize the free acids in 1 gram of sample.

The reaction mixture is then cooled to a temperature of about 60° to 90° C., preferably, 75° C., while maintaining the vacuum with a continuous nitrogen sparge, for about 20 to 40 minutes.

Thereafter, the inert gas pressure is allowed to increase to substantially atmospheric pressure and an alkaline compound, is contacted with the reaction mixture in amounts sufficient to neutralize the acid catalyst. Suitable alkaline compounds can be the hydroxides and carbonates of potassium, sodium, lithium, and ammonia, with potassium hydroxide being preferred. The pH of the reaction mixture at this stage should range from about 4.5 to about 8.0, preferably about 5.5 to 6.5.

The reaction mixture is then dried under a vacuum of about 0 to 10 mm Hg at a temperature varying from about 90° to 120° C., preferably 105° C.

The reaction product which comprises the fatty acid ester of propoxylated methyl glucoside is then filtered at a temperature of about 70° to 85° C. to produce a liquid product. The preferred ester is the stearic acid diester of a 20 mole propoxylate of methyl glucoside, and has the CTFA name PPG-20 Methyl Glucose Ether Distearate, and the CAS Registry No. 93821-74-0. The preferred diester product has a saponification value of about 55 to 75, preferably 58 to 72, and a hydroxyl value in the range of about 45 to 75, preferably 50 to 70.

Ester value is a measure of the saponifiable esters in the material. It is calculated as the difference between the saponification value and the acid value. The saponification value is a measure of the free acid and saponifiable ester groups. It is expressed as the number of milligrams of potassium hydroxide required to neutralize the free acids and saponify the esters contained in 1 gram of the material.

Hydroxyl value is defined as the number of milligrams of potassium hydroxide necessary to neutralize the acetic acid which combines on acetylation of 1 gram of sample. It is a measure of the number of hydroxyl groups in the material.

The propoxylated methyl glucoside used in the esterification reaction can be obtained by reacting methyl glucoside having the formula:

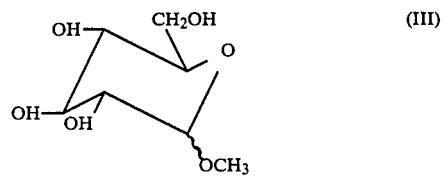

(III)

with propylene oxide, at an elevated temperature of about 160° to 175° C. in the presence of a alkaline catalyst, such as sodium methylate, or sodium hydroxide, preferably potassium hydroxide.

The preferred degree of esterification in the propoxylated glucose composition is the diester. In actuality, the esterified propoxylated methyl glucoside contains a distribution of mono-, di-, tri- and tetra esters, and virtually any degree of esterification from about 1–100% could be obtained. However, the preferred distribution of the present invention averages around the diester and the preferred fatty acids are stearic or oleic acid, with stearic acid being most preferred.

Accordingly, the molecular formula for the ester composition is:

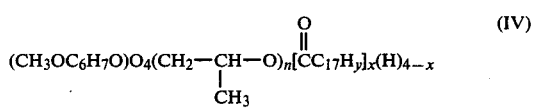

wherein n is an integer in the range of about 5 to 50, preferably about 10 to 20, and most preferably 20, x can vary from about 0.5 to 4, and y is 33 or 35. When y is 33, the ester will be the oleic acid derivative, and when y is 35, the ester will be the stearic acid derivative. When x is 2, the diester will predominate.

The PPG-20 methyl glucose ether distearate has skin moisturizing and emollient properties which make it useful in reducing transepidermal water loss from the stratum corneum of the skin. Unlike other more impervious barriers, it is not totally occlusive. This selective behavior allows for the transport of water through the barrier system for optimum rather than excessive water retention.

The key attributes of an emollient, lubrication and smoothing of the skin surface, are characteristics of PPG-20 methyl glucose ether distearate. The lubricating quality of PPG-20 methyl glucose ether distearate aids compression in pressed powders and facilitates pigment dispersion in various cosmetic preparations such as makeup and lipsticks. PPG-20 methyl glucose ether distearate is especially amenable for eye cosmetics due to its negligible Draize test score. In addition, PPG-20 methyl glucose ether distearate is nontoxic, and is not a primary dermal irritant. A typical analytical range of the properties of PPG-20 methyl glucose ether distearate appears in Table I as follows:

TABLE I

| Property | Analysis |
|---|---|
| State | liquid |
| Acid value | 2 maximum |
| Saponification value | 58–72 |
| Hydroxyl value | 50–70 |
| Arsenic | 2 ppm maximum |
| Heavy metals | 20 ppm maximum |
| Flashpoint (ASTM D 92-66, COC) | 545° F. |
| Microbiological count when packaged | Total bacteriological count (TBC) less than 10 per gram |

PPG-20 methyl glucose ether distearate is soluble in hot mineral oil, isopropyl myristate, castor oil, corn oil, ethanol and ethanol (95%). It is insoluble in water, propylene glycol and aqueous ethanol.

The safety and mildness of propoxylated methyl glucoside distearate as a cosmetic ingredient, is a most important consideration when formulating skin care and cosmetic products. Its safety data is tabulated in Table II as follows:

TABLE II

| Test | Safety Data |
|---|---|
| Acute oral toxicity - rats | $LD_{50} > 5$ g/kg |

TABLE II-continued

| Test | Safety Data |
|---|---|
| Eye irritation - rabbits | Practically non-irritating (100% concentration) |
| Primary dermal irritation - rabbits | Not a primary dermal irritant (100% concentration) |
| Comedogenic Assay | Non-comedogenic (100% concentration) |

The following Examples 1–3 provide procedures for synthesizing various propoxylated methyl glucoside distearates. Example 4 provides a transepidermal water loss study using PPG-20 methyl glucose ether distearate, and Examples 5–8 provide suggested use formulations. In the examples, all parts and percentages are by weight, unless otherwise indicated.

EXAMPLE 1

Preparation of PPG-20 Methyl Glucose Ether Distearate (n=20 based on formula IV)

While a mixture of 100.0 grams of PPG-20 methyl glucose ether and 43.1 grams of stearic acid was stirred at 70° C. under an atmosphere of nitrogen, 1.4 grams p-toluene sulfonic acid (monohydrate) was added. The resulting reaction mixture was stirred for 30 minutes at 70°–75° C. The reaction mixture was then placed under a vacuum of about 5–10 mm Hg and the temperature increased to 110° C. to distill water formed during the reaction. A slight nitrogen sparge was maintained during the vacuum distillation.

After about 3 hours at 110° C., the acid value of a sample of the reaction mixture was less than 4. The reaction mixture was then cooled to about 75° C. while under vacuum with a continuous nitrogen sparge.

When the temperature reached 75° C., the pressure was allowed to gradually increase to atmospheric and 0.93 grams of KOH (45%) was added to the reaction mixture while continuing the nitrogen sparge. The reaction mixture was then stirred for 30 minutes and had a pH (10% in IPA/$H_2O$) of between about 6 and 7.5.

The reaction mixture was then dried under a vacuum of about 0–10 mm Hg for about 1 hour at 105° C. The reaction mixture was cooled to 75°–80° C. and filtered. The reaction product, liquid PPG-20 methyl glucose ether distearate was recovered, having a saponification value of 65 and an hydroxyl value of 58.

EXAMPLE 2

Preparation of PPG-50 Methyl Glucose Ether Distearate (n=50 based upon formula IV)

565 grams of Glucam P-50, a propoxylated methyl glucoside represented by formula I where A+B+C+D=50, and 119.0 grams of stearic acid were mixed under a nitrogen atmosphere. The mixture was stirred and heated to 80° C. at which point p-toluene sulfonic acid mono-hydrate (p-TSA) (6.8 grams, 1% of total) was added. The mixture was then heated to 110° C. and reacted under vacuum of less than 1 mm Hg. The water formed from the esterification reaction was distilled off and captured in the receiver.

Vacuum distillation was continued at 110° C. for 11 hours at which point the acid value was below 4. The reaction mixture was then cooled to 80° C. Vacuum was released and 4.48 grams of KOH (45% w/w) was added to neutralize the p-TSA catalyst. The final pH (10% w/w in IPA/H₂O 50:50) of the remaining liquid product was 6.8.

The PPG-50 methyl glucose ether distearate (n=50) product was dried at 105° C. and less than 1 mm Hg. After filtration through diatomaceous earth, the yield of 661.3 grams corresponded to a 97.8% of theoretical yield. The product was filtered to give a clear, dark amber liquid with the following analytical values:

| Acid Value | 0.69 |
|---|---|
| Saponification Value | 41.59 |
| Hydroxyl Value | 41.35 |

EXAMPLE 3

Preparation of PPG-5 Methyl Glucose Ether Distearate (n=5 based upon formula IV)

517.7 grams of Glucam P-5, a propoxylated methyl glucoside represented by formula I where A+B+C+D=5, and 535.6 grams of stearic acid were mixed under a nitrogen atmosphere at 75° C. At 80° C., 7.9 grams (0.75% of total) of p-toluene sulfonic acid mono-hydrate (p-TSA) were added. The mixture was then heated to 110° C. and reacted under vacuum of less than 1 mm Hg. The water formed from the esterification reaction was distilled and captured in a receiver.

Vacuum distillation was continued at 110° C. for 12 hours at which point the acid value was below 3. The mixture was cooled to 80° C. and vacuum was released. Potassium hydroxide (5.18 grams of 45% w/w) was added to neutralize the p-TSA catalyst. After mixing for 0.5 hours the pH (10% w/w in IPA/H₂O 50:50) of the remaining liquid product was 6.9.

The PPG-5 methyl glucose ether distearate (n=5) product was dried at 105° C. with vacuum of less than 1 mm Hg for one hour. Filtration through diatomaceous earth yielded 989.9 grams (97.3% of theoretical) of a tan soft-solid wax. The product had the following analytical value:

| Acid Value | 2.07 |
|---|---|
| Saponification Value | 113.44 |
| Hydroxyl Value | 90.47 |
| Melting Temperature | 27.9° C. |

EXAMPLE 4

Transepridermal Water Loss Study 19 human subjects were treated with a test lotion containing 5% PPG-20 methyl glucose ether distearate and the same lotion (control) without PPG-20 methyl glucose ether distearate. The formulation of the test lotion and the control is as follows:

| Component | Moisturizer Weight % | |
|---|---|---|
| | Test Lotion | Control Lotion |
| Oil Phase | | |
| PPG-20 methyl glucose ether distearate | 5.0 | — |
| Glucate ® SS (Methyl glucose sesquistearate) | 0.5 | 0.5 |
| Glucamate ® SSE-20 (PEG-20 methyl glucose sesquistearate) | 1.0 | 1.0 |
| Cetyl alcohol | 0.5 | 0.5 |

-continued

| Component | Moisturizer Weight % | |
|---|---|---|
| | Test Lotion | Control Lotion |
| Water Phase | | |
| Carbopol 934 (3%) (BF Goodrich) | 6.7 | 6.7 |
| Triethanolamine (99%) | 0.2 | 0.2 |
| Water | 86.1 | 91.1 |
| TOTAL | 100.0% | 100.0% |

The moisturizer lotions were formulated as above with both phases of each lotion being heated to 65° C. The water phase was added to the oil phase at 65° C. with moderate agitation. Agitation was continued while cooling to 30°-35° C. and each of the lotions was packaged for use.

The test subjects consisted of 19 women between the ages of 23 and 57, with an average age of 34. Each of the women participating in the test were free of skin disease and, except for birth control medication, took no other medicine during the test.

The duration of the test study was 2 weeks. The test site was the upper anterior surface of the thigh. For 1 week prior to the study, all subjects were instructed not to use any cosmetic preparations, including skin care products on the anterior thighs. Both thighs were washed with soap, morning and evening. On the second week, the thighs were washed with soap in the same manner as in the first week. The thigh areas were then randomized as to right or left, with one being designated the test side and the other the control side. Each of the designated lotions were applied only to the designated sides, twice a day, morning and evening.

On the fifth day of the second week of the test, subjects reported for transepidermal water loss (TEWL) measurement 4 hours after the morning application. The area chosen for the TEWL determination was the same area for each leg which served for the basal rate determination.

The system for measuring transepidermal water loss consisted of a source of dry nitrogen at 5 psi connected to a Fisher-Porter flow meter regulated at 80 ml/min. The nitrogen was conducted into a stainless steel chamber, having an area of 16 square centimeters, and then into a Dewall Model 911 (EG&G) Dewpoint Analyzer. The effluent nitrogen was monitored with an identical Fisher-Porter Flow Meter. All fittings were of stainless steel or glass and the connection tubing was Teflon 4 mm O.D. and 2 mm I.D. The chamber was placed on the skin and held in place with a slight pressure equal to the weight of the chamber. A YSI Model 401 Thermistor was fitted into the top of the chamber to monitor the chamber temperature. Skin temperature was monitored with a YSI Probe Number 421. Temperature was read on a YSIK Model 46 telethermometer.

All rates were calculated in milligrams of water per square centimeter per hour (mg cm$^{-2}$ hr$^{-1}$), using the following relationships:

$$TEWL \text{ in mg cm}^{-2} \text{ hr}^{-1} = \frac{R.H.}{100} \times F \times D \times \frac{1}{A}$$

where:

$R.H.$ = relative humidity

-continued $$= \frac{\text{water vapor pressure in mm Hg at dewpoint temperature}}{\text{water vapor pressure in mm Hg at chamber temperature}}$$

F=flow rate in liters per hour
D=milligrams of water per liter at chamber temperature
A=chamber area in square centimeters The nitrogen used in this study was regulated at 20% relative humidity and monitored before and after the subject was studied. TEWL vaues when the product was applied were compared with TEWL values observed in the absence of any product by calculating the percentage reduction in the TEWL caused by product application as follows:

% reduction in TEWL caused by the product application =

$$\frac{(TEWL \text{ without product}) - (TEWL \text{ with product}) \times 100\%}{(TEWL \text{ without product})}$$

The percentage reduction values were collected for calculation of their mean values, and standard error of the means, as a function of the type of product applied. The calculations were performed in the usual way described in textbooks on elementary statistics which would be known to one of ordinary skill in the art.

Table III which follows, shows the total percent reduction of the TEWL of the lotion containing the PPG-20 methyl glucose ether distearate as compared with the control lotion for each of the 19 subjects.

TABLE III

| | TOTAL TEWL MEASUREMENT (%) | |
|---|---|---|
| Subject # | PPG-20 Methyl Glucose Ether Distearate Lotion | Control |
| 1 | 22.99 | 45.37 |
| 2 | 23.86 | 24.17 |
| 3 | 1.35 | −1.49 |
| 4 | 18.24 | −16.36 |
| 5 | 10.61 | −25.83 |
| 6 | 21.10 | 3.26 |
| 7 | 21.29 | 27.58 |
| 8 | 24.22 | 7.88 |
| 9 | −9.33 | −27.99 |
| 10 | −1.27 | 11.20 |
| 11 | −7.25 | −2.31 |
| 12 | −0.18 | −68.95 |
| 13 | −0.95 | −8.70 |
| 14 | 44.09 | 14.86 |
| 15 | 1.96 | −6.26 |
| 16 | 33.05 | 22.25 |
| 17 | 27.87 | 8.65 |
| 18 | 5.74 | −28.67 |
| 19 | −12.25 | −6.52 |
| Mean | 11.85 | −1.47 |
| S.E. | 3.63 | 5.88 |

As can be seen from the results in Table III, the lotion containing PPG-20 methyl glucose ether distearate reduced the TEWL by 11.85% over the basal rate. The control lotion had a negligible effect on the TEWL. These results demonstrate the efficacy of PPG-20 methyl glucose ether distearate as a barrier for reducing water loss from the stratum corneum.

In addition, microscopic examination of the treated skin showed that the area treated with PPG-20 methyl glucose ether distearate had a smoother and plumper topography. The treated skin also appeared smoother and softer than the control site.

EXAMPLE 5

Dry Skin Cream Formulation

| Component | Weight % |
|---|---|
| Oil Phase | |
| PPG-20 methyl glucose ether distearate | 2.0 |
| Cetearyl Alcohol (and) Ceteareth-20 (PROMULGEN ® D)* | 0.7 |
| Methyl Glucose Dioleate (GLUCATE ® DO)* | 0.5 |
| Cetyl Acetate (and) Acetylated Lanolin Alcohol (ACETULAN)* | 2.0 |
| Cetyl Alcohol | 1.0 |
| Stearic Acid | 4.0 |
| Mineral Oil, 70 vis. | 5.0 |
| Cetyl Palmitate | 1.0 |
| Water Phase | |
| Carbomer 934 | 0.3 |
| Triethanolamine (10% aq.) | 17.0 |
| Water | 66.5 |
| Perfume and Preservative | q.s. |

*PROMULGEN D, GLUCATE DO, and ACETULAN are trademarks of products sold by Amerchol Corporation, Edison, NJ.

Disperse the Carbomer 934 in water with vigorous agitation. Heat the oil and water phases, minus the triethanolamine, to 85° C. Add the water phase to the oil phase with moderate agitation. Immediately add the triethanolamine. Mix while cooling to room temperature. Add perfume at 40° C.

EXAMPLE 6

Pressed Powder Eye Shadow Formulation

| Component | Weight % |
|---|---|
| PPG-20 methyl glucose ether distearate | 10.0 |
| Kaolin | 10.0 |
| Talc | 26.0 |
| Mica (and) Iron Oxides (and) Titanium Dioxide (Cloisonne Golden Bronze) | 50.0 |
| Iron Oxides (Black) | 2.0 |
| Iron Oxides (Umber) | 2.0 |
| Preservative | q.s. |

Weigh all ingredients, except for the PPG-20 methyl glucose ether distearate (binder) and Cloisonne. Mix well until homogeneous. Slowly spray or add mixture to the binder dropwise. Pulverize well. Blend in Cloisonne until uniform. Press into pans using 700–1,000 lbs. pressure.

EXAMPLE 7

Soft Cream Makeup Formulation

| Component | Weight % |
|---|---|
| Oil Phase | |
| PPG-20 methyl glucose ether distearate | 4.0 |
| Mineral Oil | 10.0 |
| Stearic Acid | 4.0 |
| Cetyl Acetate (and) Acetylated Lanolin Alcohol (ACETULAN ®)* | 3.4 |
| Glyceryl Stearate, S.E. | 4.0 |
| Water Phase | |
| Deionized Water | 32.0 |
| Methyl Gluceth-10 (GLUCAM ® E-10)* | 5.0 |
| Triethanolamine (98%) | 1.5 |
| PEG-8 Stearate | 0.5 |
| Cellulose Gum | 0.5 |
| Magnesium Aluminum Silicate (4% slurry) | 25.0 |

| Component | Weight % |
|---|---|
| Pigment Phase | |
| Iron Oxides, Talc, Titanium Dioxide | 10.0 |
| Perfume and Preservative | q.s. |

*ACETULAN AND GLUCAM E-10 are trademarks of products sold by Amerchol Corporation, Edison, NJ.

Sprinkle cellulose gum and magnesium aluminum silicate into heated water phase with constant agitation. Maintain temperature and mix until homogeneous. Add pigment phase and pass through colloid mill. Heat to 70° C. and add oil phase (previously heated to 70° C.). Cool to room temperature with slow mixing.

EXAMPLE 8

Moisturizing Lotion Formulation

| | |
|---|---|
| PPG-20 methyl glucose ether distearate | 4.0 |
| Methyl Glucose Sesquistearate (GLUCATE ® SS)* | 0.5 |
| PEG-20 Methyl Glucose Sesquistearate (GLUCAMATE ® SSE-20)* | 1.5 |
| Cetyl Alcohol | 0.5 |
| Mineral Oil | 2.0 |
| Water Phase | |
| Carbomer 934 (3% aq. slurry) | 10.0 |
| Water | 78.5 |
| Triethanolamine (10% aq.) | 3.0 |
| Perfume and Preservative | q.s. |

*GLUCATE SS and GLUCAMATE SSE-20 are trademarks of products sold by Amerchol Corporation, Edison, NJ.

Heat oil and water phases, minus the triethanolamine, to 75° C. Add the water phase to the oil phase with good agitation. Add triethanolamine after emulsion has formed. Mix while cooling to room temperature. Add perfume below 40° C.

What is claimed is:

1. A fatty acid ester of propoxylated methyl glucoside represented by the structural formula:

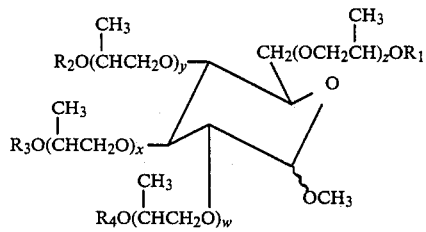

wherein:
w+x+y+z is from about 5 to 50; and
each $R_1$, $R_2$, $R_3$ and $R_4$ is individually hydrogen or

wherein M is a $C_{11}$-$C_{29}$ alkyl or alkenyl, provided that at least one $R_1$, $R_2$, $R_3$ or $R_4$ is

2. The compound of claim 1, wherein W+X+Y+Z equals about 10 to 20.

3. The compound of claim 2, wherein W+X+Y+Z equals about 20.

4. The compound of claim 1, wherein the fatty acid ester is the ester of a fatty acid selected from the group consisting of stearic acid, linoleic acid, oleic acid, lauric acid, palmitic acid, linolenic acid and linseed oil acid.

5. The compound of claim 4, wherein the fatty acid ester is the ester of stearic acid.

6. The compound of claim 5 wherein the degree of esterification averages about the diester.

7. The compound of claim 6, having a saponification value of about 58 to 72, and a hydroxyl value of about 50 to 70.

8. A process for preparing an esterified propoxylated methyl glucoside, comprising:
reacting a propoxylated methyl glucoside having the formula:

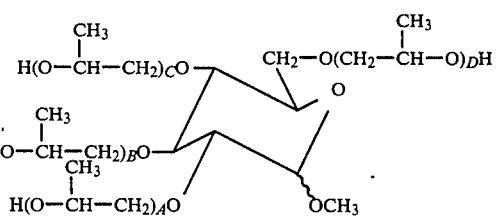

wherein A+B+C+D is about 5 to 50, with a fatty acid at a temperature of about 100°-120° C. to produce said esterified propoxylated methyl glucoside having the formula:

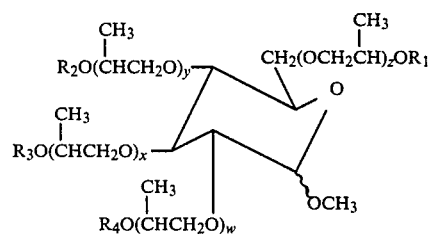

wherein W+X+Y+Z varies from about 5 to 50, and wherein any one of $R_1$, $R_2$, $R_3$ and $R_4$ can be H or

wherein M is $C_{11}$-$C_{29}$ alkyl or alkenyl, and at least one of $R_1$, $R_2$, $R_3$ and $R_4$ is

9. The process of claim 8, wherein A+B+C+D is about 10 to 20 and W+X+Y+Z is about 10 to 20.

10. The process of claim 8, wherein

is derived from at least one fatty acid selected from the group consisting of stearic acid, linoleic acid, oleic acid, lauric acid, palmitic acid, linolenic acid, and linseed oil acid.

11. The process of claim 10, wherein said fatty acid is stearic acid.

12. The distearate product formed by the process of claim 11, having a saponification value of about 58 to 72 and a hydroxyl value of about 50 to 70.

13. The process of claim 11, wherein the reaction is conducted in the presence of an acid catalyst selected from the group consisting of toluene sulfonic acid, sulfuric acid, phosphoric acid, $SO_2$, $H_3BO_3$, a Lewis acid, and oxalic acid.

14. The process of claim 13, wherein the acid catalyst is toluene sulfonic acid.

15. The process of claim 8, wherein the reaction is conducted in an inert atmosphere, selected from the group consisting of nitrogen, argon, helium, and mixtures thereof.

16. The process of claim 15, wherein the inert atmosphere comprises nitrogen.

17. The process of claim 8, wherein the reactants are initially contacted and heated to a temperature of about 50° to 90° C. until homogeneity of the reaction mixture occurs.

18. The process of claim 17, wherein heating is conducted at a temperature of 100° to 120° C. under vacuum, until the acid value is below 5.

19. The process of claim 18, wherein the reaction mixture is then cooled to a temperature of about 60° to 90° C. and the pH is adjusted to a range of about 4.5 to 8.

20. The process of claim 19, wherein the pH is adjusted to a range of about 5.5 to 6.5.

21. The process of claim 19, wherein the reaction mixture is dried under vacuum at a temperature of about 90° to 120° C.

22. The process of claim 21, wherein the reaction mixture is filtered at a temperature of about 70° to 85° C.

23. A compound produced by the process of claim 14.

24. A topical skin care composition having moisturizing and emollient properties comprising an effective amount of a fatty acid ester of propoxylated methyl glucoside represented by the structural formula:

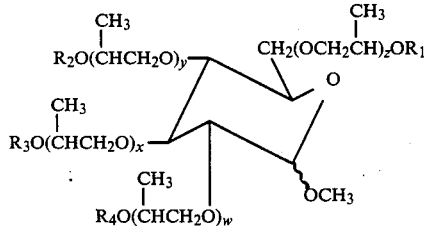

wherein:

$w+x+y+z$ is from about 5 to 50; and
each $R_1$, $R_2$, $R_3$ and $R_4$ is individually hydrogen or

wherein M is a $C_{11}$–$C_{29}$ alkyl or alkenyl, provided that at least one $R_1$, $R_2$, $R_3$ or $R_4$ is

in combination with cosmetically suitable ingredients.

25. The composition of claim 24, wherein the average mole ratio varies from about 10 to 20, respectively.

26. The composition of claim 25, wherein the average mole ratio is about 20.

27. The composition of claim 24, wherein the fatty acid ester is the ester of a fatty acid selected from the group consisting of stearic acid, linoleic acid, oleic acid, lauric acid, palmitic acid, linolenic acid and linseed oil acid.

28. The composition of claim 27, wherein the fatty acid ester is the ester of stearic acid.

29. The composition of claim 28, wherein the degree of esterification averages about the diester.

30. The composition of claim 24, including a minor oil phase portion of less than about 25% by weight of the composition, wherein said minor oil phase portion contains the fatty acid ester of propoxylated methyl glucoside in an amount varying from about 0.5 to 5% by weight of the total formulation.

31. The composition of claim 24, in the form of a dry skin cream.

32. The composition of claim 24, in the form of a pressed powder eye shadow.

33. The composition of claim 24, in the form of a soft cream makeup.

34. The composition of claim 24, in the form of a moisturizer.

35. A method for reducing the transepidermal water loss from the stratum corneum of the skin comprising contacting the skin with an effective amount of a fatty acid ester of propoxylated methyl glucoside in combination with cosmetically acceptable ingredients.

36. The method of claim 35, wherein the fatty acid ester is the ester of a fatty acid selected from the group consisting of stearic acid, linoleic acid, oleic acid, lauric acid, palmitic acid, linolenic acid and linseed oil acid.

37. The method of claim 36, wherein the fatty acid ester is the ester of stearic acid.

38. The method of claim 37, wherein the degree of esterification averages about the diester.

* * * * *